US005772656A

United States Patent [19]
Klopotek

[11] Patent Number: 5,772,656
[45] Date of Patent: Jun. 30, 1998

[54] CALIBRATION APPARATUS FOR LASER ABLATIVE SYSTEMS

[75] Inventor: Peter J. Klopotek, Framingham, Mass.

[73] Assignee: Summit Technology, Inc., Waltham, Mass.

[21] Appl. No.: 483,569

[22] Filed: Jun. 7, 1995

Related U.S. Application Data

[63] Continuation of Ser. No. 72,505, Jun. 4, 1993, abandoned.
[51] Int. Cl.[6] ........................................ A61N 5/06
[52] U.S. Cl. .................................. 606/12; 606/5; 606/10; 606/13; 219/121.6; 250/252.1; 250/583; 250/363.9; 250/372; 250/205.5; 250/472.1; 250/504 R; 356/51; 356/72; 356/389; 356/394; 356/432
[58] Field of Search ...................................... 128/897, 898; 606/2, 2.5, 3–19; 219/121.6, 121.83, 121.73–121.75; 250/252.1, 316.1, 580–586, 589, 328, 359, 336.2, 339.1, 339.2, 361 R, 363.9, 372, 200, 201.2, 201.5, 548, 472.1, 473.1, 474.1, 475.2, 491.1, 503.1, 504 R; 356/51, 72, 121, 124.1–127, 381, 382, 388–394, 432–435

[56] References Cited

U.S. PATENT DOCUMENTS

| | | |
|---|---|---|
| 3,262,122 | 7/1966 | Fleisher et al. . |
| 3,364,493 | 1/1968 | Myer . |
| 3,558,208 | 1/1971 | Hudson . |
| 3,665,483 | 5/1972 | Becker et al. . |
| 4,139,409 | 2/1979 | Macken et al. . |
| 4,388,517 | 6/1983 | Schulte et al. . |
| 4,414,059 | 11/1983 | Blum et al. . |
| 4,461,294 | 7/1984 | Baron . |
| 4,648,400 | 3/1987 | Schneider et al. . |
| 4,686,979 | 8/1987 | Gruen et al. . |

(List continued on next page.)

FOREIGN PATENT DOCUMENTS

| | | |
|---|---|---|
| 0 050 159 A1 | 4/1982 | European Pat. Off. . |
| 38 41 244 A1 | 6/1990 | Germany . |
| WO 87 05496 | 9/1987 | WIPO . |
| 9222255 | 12/1992 | WIPO ...................................... 606/12 |

OTHER PUBLICATIONS

J.P. Coullahan, et al., (1979), "Chip Passivation Technique", *IBM Technical Disclosure Bulletin*, 22(6), pp. 2279–2281.
C.A. Puliafito, M.D., et al., (1985), "Excimer Laser Ablation of the Cornea and Lens,". *Ophthalmogy*, 92(6), pp. 741–748.
W. Crooks & J.T. Jacobs, (1976), "Microfilm by Laser Imaging Employing Sublimable Dyes", *IBM Technical Bulletin*, 19(1), p. 285.
S.B. Rosenbaum & J.M. Schiller, (1976), "Coating Protection for Laser Cutting and Welding Operations", *IBM Technical Bulletin*, 18(8), p. 2531.
S. L. Trokel, M.D., et al., (1983), "Excimer Laser Surgery of Cornea", *American Journal of Ophthalmoloy*, 96(6), pp. 710–715.
D.J. O'Hara & A.D. Tencza, (1969), "Holographic Selective Heating System", *IBM Technical Disclosure Bulletin*, 11(9), pp. 1168–1169.
J. Taboda, et al., (1981), "Response of the Corneal Epithelium to KrF Excimer Laser Pulses", *Health Physics*, 40, pp. 677–683.

*Primary Examiner*—David M. Shay
*Attorney, Agent, or Firm*—Thomas J. Engellenner; Scott D. Rothenberger; Lahive & Cockfield, LLP

[57] ABSTRACT

A calibration apparatus is disclosed for measuring the properties of a laser beam. The apparatus includes a photoreactive element having a composition which reacts with laser radiation in a manner proportional to the intensity or intensity profile of the laser beam and an alignment means for disposing the photoreactive element in the path of a laser beam, such that the beam can be activate to impinge upon the photoreactive element and the properties of the beam are recorded by changes in the state of the calibration element. The calibration element may also be used to provide corrective feedback for modifying or controlling the properties of the laser beam.

45 Claims, 3 Drawing Sheets

U.S. PATENT DOCUMENTS

| | | |
|---|---|---|
| 4,732,148 | 3/1988 | L'Esperance, Jr. . |
| 4,760,537 | 7/1988 | Martin et al. . |
| 4,792,690 | 12/1988 | McCann et al. . |
| 4,797,555 | 1/1989 | La Mar . |
| 4,856,513 | 8/1989 | Muller . |
| 4,911,711 | 3/1990 | Telfour et al. ............... 606/5 |
| 4,916,319 | 4/1990 | Telfair et al. . |
| 4,941,093 | 7/1990 | Marshall et al. . |
| 4,973,330 | 11/1990 | Azema et al. . |
| 4,994,058 | 2/1991 | Raven et al. . |
| 5,019,074 | 5/1991 | Muller . |
| 5,147,352 | 9/1992 | Azema et al. . |
| 5,163,934 | 11/1992 | Munnerlyn . |
| 5,261,822 | 11/1993 | Hall et al. . |
| 5,324,281 | 6/1994 | Muller . |
| 5,464,960 | 11/1995 | Hall et al. . |

CALIBRATION APPARATUS FOR LASER ABLATIVE SYSTEMS

This application is a continuation of application Ser. No. 08/072,505 filed on Jun. 4, 1993 abandoned. The contents of all of the aforementioned applications are hereby incorporated by reference.

BACKGROUND OF THE INVENTION

The technical field of this invention is laser ablation of surfaces. In particular, the invention relates to systems and methods for measuring and recording the properties of laser ablation systems.

It is known to employ lasers to erode surfaces of workpieces. Recently, lasers have also been used as surgical devices. The ability of certain lasers to reprofile biological materials has created major new opportunities for corrective and/or cosmetic operations. For example, a variety of lasers emitting high intensity, rapidly pulsed radiation are currently being investigated for use in corneal reprofiling procedures to change the shape of the cornea and, thereby, correct refractive vision disorders, such as myopia (nearsightedness), hyperopia (farsightedness) and astigmatisms (deviations from spherical symmetry).

Ablative laser radiation is also being studied for various other surgical purposes, including arthroscopic surgery, angioplasty, treatment of skin diseases and dentistry. Moreover, ablative laser systems are becoming increasingly commonplace in non-surgical applications, such as the micromachining of electronic components and other industrial processes.

In most laser ablative procedures, precise control of the laser beam parameters, including the initial spatial beam profile, and any homogenizing, focusing or beamshaping operations are critical to success in reprofiling a target surface. This is especially true in biological reprofiling procedures, such as photorefractive keratectomy (PRK) where layers of corneal tissue only a few microns in thickness are to be ablated.

Various methods for monitoring laser ablative procedures have been proposed. For example, a feedback control system for PRK operations is described in the U.S. Pat. No. 4,941,093 to Marshall et al. In this system, a keratometer forms part of laser ablation apparatus and continually measures the curvature of the cornea to compare actually observed conditions with predicted values. The amount of energy required to ablate a desired amount of material from the target element is first calculated. The laser is then directed to supply an amount of energy slightly less than this calculated amount to allow for deviation in the predicted response of the element to the laser energy and for deviations in the ablation system. The steps of measuring a parameter and applying energy are repeated until the optical element is reshaped within predetermined tolerance limits. One drawback with this approach is the additional time necessary to complete the iterative process which prolongs the operation and increases the risk of misalignment occurring.

Another disadvantage with feedback control systems based on reflective optical measurements is the lack of a physical record of the ablative properties of the laser and beamshaping/focusing system. Such a record can provide a baseline for comparing the operation of the ablation system from one usage to another and for correcting errors before the system is put into use on a patient. Further, should a problem arise after a procedure is completed, a physical record of the output of the laser and beamshaping/focusing elements would be of use in determining whether the proper protocol was followed by the clinician.

Thus, it is an object of the present invention to provide an apparatus and method for analytically determining the initial conditions of a laser ablation system and for creating a physical record of the ablative properties of the ablation system.

It is also an object of the present invention to incorporate analysis and feedback apparatus and methods to control the laser ablation system based on the physical properties of a physical record.

SUMMARY OF THE INVENTION

A calibration apparatus is disclosed for measuring the properties of a laser beam. The apparatus includes a photoreactive element having a composition which reacts with laser radiation in a manner dependent upon the intensity or intensity profile of the laser beam and an alignment means for disposing the photoreactive element in the path of a laser beam, such that the beam can be activated to impinge upon the photoreactive element and the properties of the beam are recorded by changes in the state of the photoreactive element.

In one embodiment, the photoreactive element is an erodable element formed from a erodable material having ablation characteristics similar to that of biological tissue, such that the calibration apparatus can be used to ensure that surgical laser apparatus is operating within desired parameters.

The invention is particularly useful in connection with corneal surgical systems for performing photorefractive keratectomy where the surface of the cornea is reprofiled to correct vision disorders. By employing a photoreactive element as a calibration apparatus, the parameters affecting such a corneal procedure (e.g., beam homogeneity, focusing and beam-shaping over time) can be assessed before the system is used to treat a patient's eye. Moreover, the photoreactive element provides a physical record of the laser beam profile which can be examined prior to the procedure to either confirm proper operation of the laser apparatus or to permit modification of the operating parameters either manually or by automated feedback control.

In a further aspect of the invention, the photoreactive element can include an optical indicator which is either modified or ablated by laser radiation. For example, when an erodable element is employed, this element can include an indicator substance, such as a pigment, dye or fluorescent material. As the photoreactive element is eroded to create a calibration record, the amount of the optical indicator remaining in specific portions of the element will vary depending upon the intensity and duration of exposure to the ablative radiation. These changes in the optical indicator can be detected by a simple photodetector fluroscope or camera system.

A principal advantage in using an optical indicator is that such indicators can be readily chosen for optical properties within the visible spectrum. By measuring changes in the visible, spectrum optical properties (rather than the ultraviolet radiation which is generated directly by the laser ablation system), less expensive and simpler cameras, such as simple CCD cameras, can be used to record and/or analyze the calibration records, as well as readily permit visual observation of the calibration record, itself.

In yet a further aspect of the invention, a calibration system for monitoring calibration records is disclosed, including an illumination source and a photodetector, which detects the changes in the optical indicator following exposure to the ablative laser radiation. Signals from the detector can then be transmitted to a computer or the like for storage as digital data or can be transmitted to an analyzing device to generate control or feedback signals.

In another embodiment of the invention, the photoreactive element can be a radiation-absorbing element which does not lose its physical shape upon exposure to ablative radiation but rather has optical properties which are altered. Such radiation-absorbing elements can consist of materials which are bleached, darkened or which fluoresce upon exposure to laser radiation. Again, these optical properties can be chosen to permit inspection and monitoring by photodetectors operating within the visible spectrum, and the records can be stored as digital data or analyzed to provide feedback and/or control signals.

The invention will next be described in connection with certain preferred embodiments; however, it should be clear that various additions, subtractions and modifications can be made without departing from the spirit or scope of the claims.

DETAILED DESCRIPTION

Figure 1:
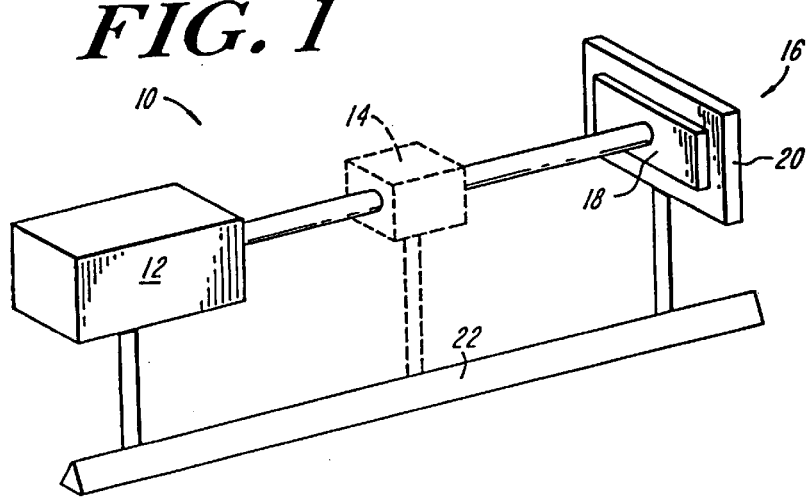
FIG. 1 is a schematic illustration of a calibration apparatus for use in calibrating a laser ablation system according to the invention.

In FIG. 1, a laser ablation system 10 with a calibration apparatus 16 is shown. As shown, system 10 includes laser 12, and, optionally, a beam-shaping assembly 14 for modifying the shape and/or size of the ablative radiation beam over time, as desired, to effect reprofiling of a surface. The calibration apparatus 16 can include a photoreactive element 18 and a mounting means 20, as shown. Each of the elements 12, 14 and 16 are preferably connected via an alignment element 21 onto an optical rail 22 or the like in order to maintain alignment during the calibration process.

The calibration apparatus 16 can take various forms, including the two-layer, plastic block shown in FIG. 1. The layer 18 is preferably formed of a photoreactive material having a composition which reacts with laser radiation in a manner proportional to the intensity profile of the laser beam. This photoreactive element 18 can be mounted upon a non-reactive carrier or mounting element 20, as shown.

This backing 20 can be optically transparent or reflective to assist in optical read-out of the calibration records.

Examples of transparent backing materials include glass, quartz and optically-transparent plastics. Depending upon the laser undergoing calibration, the transparent backing should be capable of transmitting radiation throughout at least a portion of the spectrum from about 180 to about 1200 nanometers. For read-out purposes, it is preferable that the transparent backing be transmissive not only in the region of the ablative radiation but also in at least a portion of the spectrum from about 450 nanometers to about 900 nanometers to permit the use of visible light in displaying or measuring the calibration record. In any event, the transparent backing should be optically homogeneous, well characterized and stable over time.

Reflective backing materials can be formed from similar materials with reflective metal coatings or the like. For reasons similar to those expressed above for transparent backings, a broadband reflector is preferable to permit the use of visible light for read-out purposes. In some applications, reflectance of the ablative radiation wavelength may not be necessary at all, so long as visible light can be reflected by the material following recording.

Alternatively, a single layer structure can be employed with the photoreactive element serving to provide a record of the laser radiation, itself, so long as it has sufficient thickness and/or strength to ensure that structural integrity is maintained following irradiation.

Figure 2:
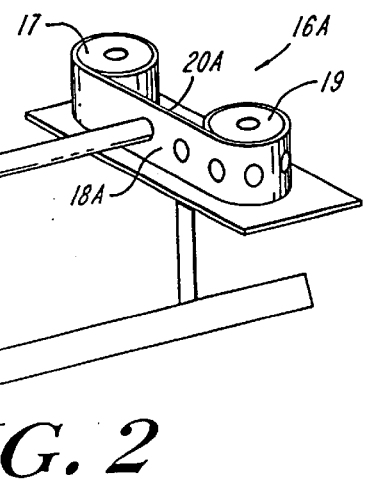
FIG. 2 schematic illustration of another calibration apparatus according to the invention.

An alternative calibration apparatus 16A is shown in FIG. 2 where the plastic block of FIG. 1 has been replaced with a tape apparatus 21A, including mechanized tape transport reels 17 and 19 which serve to align the tape with the laser beam and transport the tape across the beam path, such that a "snapshot" can be taken of the beam profile, (e.g., a recording of the intensity profile effected by a series of ablative pulses during a time period, or frame, of predefined duration). Again, the calibration apparatus 16A (shown in FIG. 2) can be constructed into two layers: a photoreactive layer 18A and a carrier tape layer 20A. Alternatively, the tape can include a transparent or reflective, non-reactive material having photoreactive elements incorporated therein.

In one embodiment, the photoreactive element can be an erodable element, for example, a polymeric block or tape having a thickness of about 10 micrometers to about 100 micrometers, preferably from about 25 micrometers to about 75 micrometers, which is ablated by the laser radiation to create a physical record of the laser radiation. This erodable element can further included an optical indicator, which is lost during the ablation process, such that those regions of the calibration record which are ablated will be either less saturated in color or, otherwise, modified in terms of transparency or absorptivity. The optical indicator can be an indicator substance chosen from the group consisting of pigments, dyes and fluorescent substances. Alternatively, the photoreactive element can be a radiation-absorbing element, which does not lose its physical shape upon exposure to the ablative radiation but rather has optical properties which are altered. Such radiation-absorbing elements can consist of materials which are bleached, darkened or subject to fluorescence upon exposure to laser radiation.

One preferred material for an erodable calibration record is a polymeric coating of polymethylmethacrylate (PMMA), polymethylstyrene, polycarbonate or mixtures thereof. For example, suitable polycarbonate calibration records can be fabricated from LEXAN® resins, (commercially available from General Electric, Pittsfield, Mass.) or from CR-39® resins (PPG Industries, Pittsburgh, Pa.). Conveniently, the erodable calibration record can have similar ablation characteristics to biological tissue, particularly when the laser ablation system is directed to use in reprofiling biological materials, such as the ocular cornea. The absorption coefficient of such erodable, polymeric calibration records can range from about $10^3$ cm$^{-1}$ to about $10^6$ cm$^{-1}$. The polymeric record can be treated for colorimetric analysis by adding a dye or other colorant either during polymerization or via diffusion after polymerization. Diffusioned dye (assisted by heating or pressurization) can be advantageous because it permits the dye to be distributed in a non-linear fashion relative to the thickness of the record. In some applications, this non-linear distribution is preferred for read-out purposes.

Figure 3:
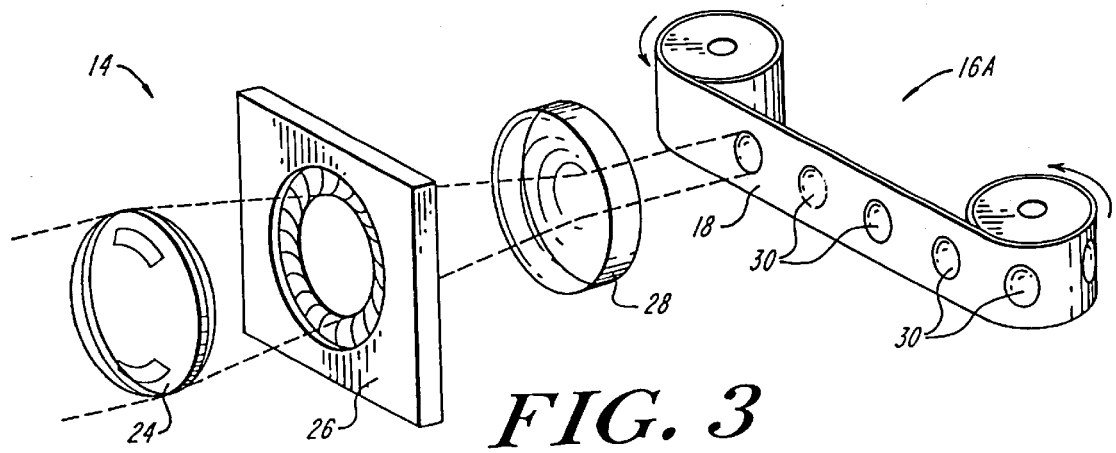
FIG. 3 is a more detailed schematic illustration of a beam-shaping assembly and calibration apparatus for use in the system of FIG. 2.

In FIG. 3, an embodiment of a beam-shaping assembly 14 suitable for use in the system 10 is shown in more detail in conjunction with a tape-transport calibration apparatus 16A. As shown, the beam-shaping assembly includes a first convex lens 24, an adjustable iris 26, and a concave lens 28. Together, these elements cooperate to produce an ablative radiation beam, which can be varied in cross-sectional area over time. By progressively opening the iris 26, an ablation pattern will be presented to the target surface in which the greatest ablative energy impinges upon a central region of the target and progressively decreases to the periphery. When such an ablation profile is applied to a convex surface, such as the cornea of an eye, the result is a reprofiling effect that serves to flatten the curvature of the surface. In this manner, myopia, a common vision disorder can be corrected by reprofiling the cornea. Thus, the calibration apparatus 16A, shown in FIG. 3, can be used to determine whether the laser beam and the beam-shaping assembly 14A are properly configured to affect the desired ablation profile. By disposing the calibration apparatus 16A within the beam path and then varying the opening of the aperture 26 in accordance with the planned procedure, an ablation record 30 will be created in the photoreactive element 18.

Figure 4A:
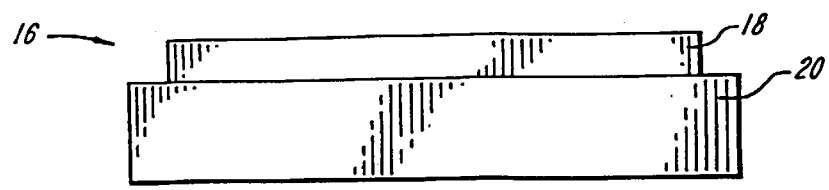
FIGS. 4A an 4B illustrate one embodiment of a calibration record before and after exposure to ablative radiation, respectively, in a calibration system according to the invention.
Figure 4B:
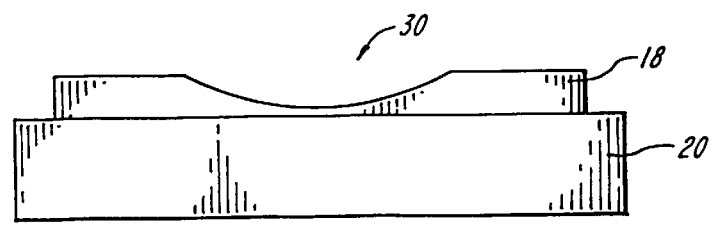

FIGS. 4A and 4B further illustrate this process schematically. As shown in FIG. 4A, the calibration apparatus can include a photoreactive (e.g., erodable) layer 18 and a carrier 20 (e.g., a transparent block of material or a transparent tape carrier). Prior to exposure to ablative radiation, the calibration apparatus in FIG. 4A has a uniform and planar surface. Following to exposure to laser radiation, as shown in FIG. 4B, a calibration record 30 has been created by the ablative action of the laser radiation upon the photoreactive element 18.

Figure 5:
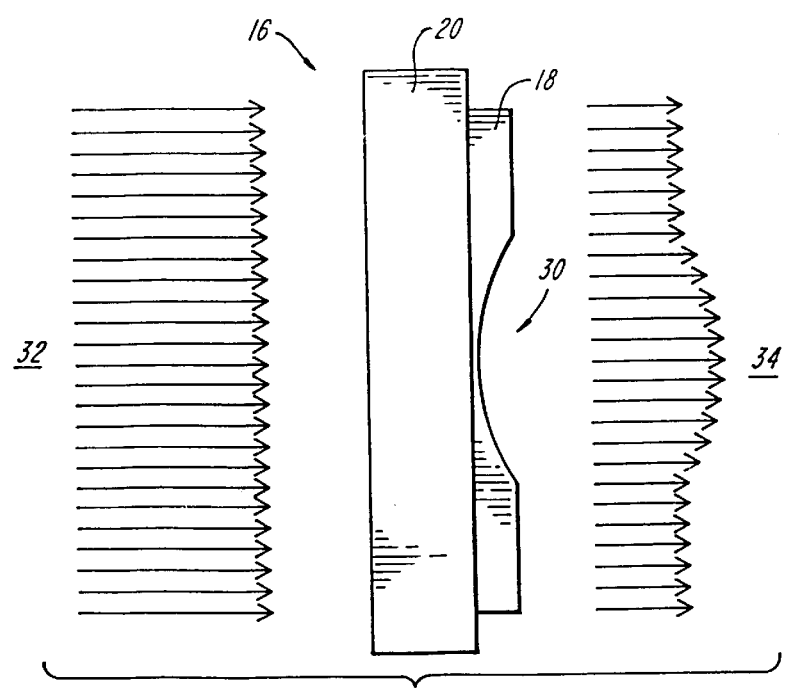
FIG. 5 is a schematic illustration of how a calibration record can be read optically.

FIG. 5 illustrates how this calibration record can be monitored or interpreted optically. Once the calibration record has been created in the photoreactive element 18, it can be subjected to illuminating light 32. As the "read out" light passes through the calibration record, it is modified by the optical properties of the record, itself, such that a modified light beam 34 emerges. As noted above, the optical properties which can be modified include, color, absorptivity, fluorescence and the like.

Figure 6:
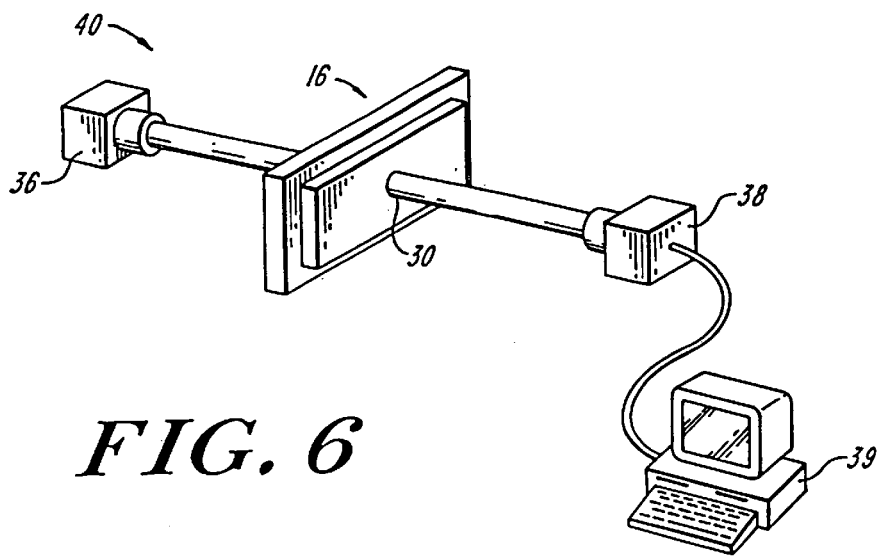
FIG. 6 is a schematic illustration of a monitoring system for reading calibration records according to the invention.

In FIG. 6, calibration system 40 is shown for reading the calibration apparatus 16 and records 30 contained thereon. As shown, the system 40 includes a light source 36 emitting light which can be either spatially or temporally coherent or non-coherent and a detector 38 for measuring the intensity profile of the light transmitted through the calibration record. The detector 38 can further be coupled to a computer storage system 39 for digital storage of the calibration data and/or analysis thereof.

Figure 7:
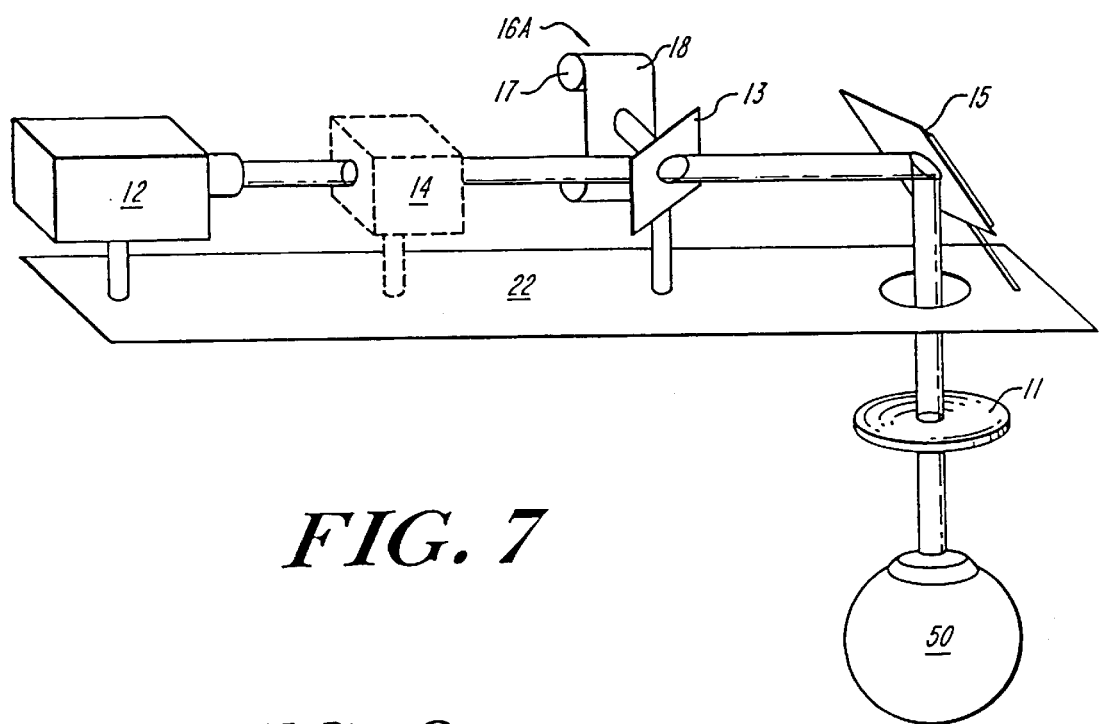
FIG. 7 is a schematic illustration of another embodiment of a calibration apparatus for use in a laser ablation system according to the invention.

In FIG. 7, another embodiment of a laser ablation system employing a calibration apparatus is shown. In the embodiment of FIG. 7, a calibration record can be made simultaneously with the ablation procedure. As shown, the system includes a laser 12 beam-shaping assembly 14 and tape calibration apparatus 16A, which is disposed at an angle to the beam path. A beam-splitting mirror 13, which preferably is movable and adjustable, can be disposed within the path and diverts a portion of the ablative radiation beam to the calibration apparatus 16A. The remainder of the beam is transmitted via mirror 15 and imaging lens 11 to the target, e.g., the cornea of an eye 50. The beam-shaping mirror 13 can be chosen to reflect only a small portion of the ablative radiation, and the photoreactive element 18 of the calibration apparatus 16A can be chosen from materials which are very sensitive to the ablative radiation, such that only a small fraction of the total beam energy is necessary in order to create a calibration record.

Figure 8:
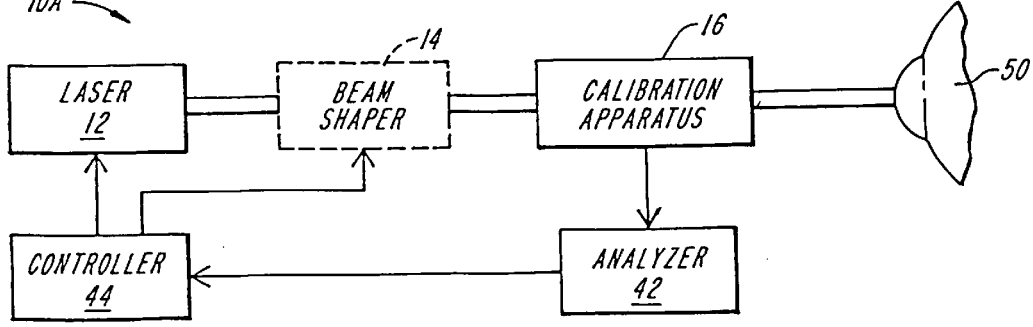
FIG. 8 is a block diagram of a laser ablation system incorporating the calibration apparatus of the present invention for feedback control.

In FIG. 8, an overall ablation system 10A employing a calibration apparatus as part of a feedback control mechanism. As shown, the system 10A includes a laser, generating a beam of ablative radiation for reprofiling a surface 50, such as the cornea of an eye. The system further includes a beam-shaping assembly 14, a calibration apparatus 16, an analyzer 42 and a controller 44. As shown, the laser radiation beam, itself, or the output of the beam-shaping assembly 14 can be monitored by the calibration apparatus prior to commencement of the corneal reshaping procedure. If the ablation apparatus determines that the beam shape is correct, the calibration apparatus can be removed from the optical beam path, and the procedure begins. If on the other hand, the calibration apparatus creates a record which the analyzer 42 determines to be unsatisfactory, a feedback control signal is transmitted via controller 44 to the laser or beam shaper in order to effect correction of one or more parameters. The procedure is then repeated until the calibration apparatus indicates that the desired profile will be achieved.

What is claimed is:

1. An apparatus for measuring the properties of a surgical laser beam comprising a photoreactive element having a composition including at least one layer of dye-impregnated material having a non-uniform distribution of dye through the layer which reacts with laser radiation in a manner dependent upon an intensity profile of the laser beam and an optical sensing element for determining changes in the beam.

2. The apparatus of claim 1, wherein the photoreactive element comprises an erodable element which is ablated by laser radiation in a manner proportional to the intensity profile of the beam.

3. The apparatus of claim 1, wherein the photoreactive element comprises a radiation-absorbing element having optical properties, which are altered by laser radiation in a manner proportional to the intensity profile of the beam.

4. The apparatus of claim 3, wherein the radiating-absorbing element exhibits fluorescence in response to radiation.

5. The apparatus of claim 3, wherein the radiation-absorbing element is bleached in response to radiation.

6. The apparatus of claim 3, wherein the radiation absorbing element is darkened in response to radiation.

7. The apparatus of claim 3, wherein the radiation absorbing element changes color in response to radiation.

8. The apparatus of claim 3, wherein the radiation absorbing element changes in color intensity in response to radiation.

9. A system for measuring the properties of a surgical laser beam comprising:

a beam splitter disposed within a path of a surgical laser beam for splitting off a component of the beam for analysis;

a photoreactive element disposed to receive the component of the beam having a composition including at least one layer of dye-impregnated material having a non-uniform distribution of dye through the layer which reacts with laser radiation in a manner dependent upon an intensity profile of a laser beam; and a readout means coupled to the photoreactive element for detecting changes in the photoreactive element as a measurement of the intensity profile of the laser beam.

10. The system of claim 9 further comprising:

an alignment means for disposing said photoreactive element in the path of the component of the laser beam, such that the component of the beam can be activated to impinge upon the photoreactive element and a plurality of properties of the beam are recorded by changes in the state of the photoreactive element.

11. The system of claim 9, wherein the readout means further comprises a photodetector for capturing an image of the photoreactive element and the system further comprises:

a recorder for recording the image to provide a record of the intensity profile of the beam simultaneously with a surgical procedure.

12. The system of claim 9, wherein the photoreactive element further comprises an erodable element which is ablated by laser radiation in a manner proportional to the intensity profile of the beam.

13. The system of claim 9, wherein the readout means further comprises a photodetector for capturing an image of the photoreactive element and the system further comprises:

a digitizer for transforming the image into digital data.

14. The system of claim 13 further comprising:

a calibration means for comparing the digital data with stored pre-determined parameters of an ideal beam for a surgical procedure to determine whether the beam is within an acceptable range for surgical procedure.

15. The system of claim 9, wherein the readout means further comprises a photodetector for capturing an image of the photoreactive element and the system further comprises:

a digital data processor for transforming the image into digital data and for comparing the digital data with stored pre-determined parameters of an ideal beam for a surgical procedure.

16. The system of claim 15 further comprising:

a controller to transmit feed-back signals to a laser controller to modify the laser based on the results of the comparison.

17. The system of claim 9, wherein the photoreactive element further comprises a radiation-absorbing element having optical properties, which are altered by laser radiation in a manner proportional to the intensity profile of the beam.

18. The system of claim 17, wherein the radiating-absorbing element exhibits fluorescence in response to radiation.

19. The system of claim 17, wherein the radiation-absorbing element is bleached in response to radiation.

20. The system of claim 17, wherein the radiation absorbing element is darkened in response to radiation.

21. The system of claim 17, wherein the radiation absorbing element changes color in response to radiation.

22. The system of claim 17, wherein the radiation absorbing element changes in color intensity in response to radiation.

23. The system of claim 9, wherein the photoreactive element has a plurality of recording locations, such that the properties of the beam are recorded by changes in a state of the photoreactive element at the recording locations, and the system further comprises:

an adjustable alignment means for aligning different segments of the photoreactive element in a path of the component of the laser beam, such the component of the beam can be activated to impinge upon a plurality of locations and thereby record multiple measurements of the component of the beam on the photoreactive element.

24. The system of claim 23, wherein the photoreactive element further comprises an optical indicator which is ablated by laser radiation.

25. The system of claim 23, wherein the optical indicator further comprises an indicator substance chosen from the group consisting of pigments, dyes and fluorescent substances.

26. The system of claim 23, wherein the photoreactive element further comprises a tape including a non-laser beam reactive material.

27. The system of claim 23, wherein the adjustable alignment means further comprises a mechanized transport for disposing the photoreactive element in the path of the component of the laser beam.

28. The system of claim 23 further comprising:

an optical recording means for reading the photoreactive element and for storing data indicative of at least one effect of the component of the laser beam on the photoreactive element.

29. The system of claim 23 further comprising:

reading means for determining said intensity profile of said laser beam by changes in said photoreactive element; and comparison means for comparing said intensity profile determined by said reading means with a prescribed intensity profile.

30. The system of claim 29 wherein the photoreactive element has optical properties which are changed by laser irradiation; and the reading means further comprises an optical sensor for capturing an image of the photoreactive element.

31. The system of claim 23, wherein the adjustable alignment means further comprises mounting element for mounting the photoreactive element in an adjustable position relative to the laser beam wherein the mounting element has a backing means to which at least one photoreactive element is attached.

32. The system of claim 31, wherein the backing means further comprises an optically transparent material chosen from the group consisting of glass, plastic and quartz.

33. The system of claim 31, wherein the backing means is an optically reflective material.

34. The system of claim 23 further comprising:

an optical sensing element for determining the properties of the beam.

35. The system of claim 34, wherein the optical sensing element further comprises a camera for capturing an image of the photoreactive element.

36. The system of claim 34, wherein the optical sensing element further comprises a fluoroscope.

37. The system of claim 34, wherein the optical sensing element further comprises a photodetector.

38. The system of claim 34 further comprising:

memory means for storing established parameters representative of an ideal beam.

39. The system of claim 38 further comprising:

a processing element for comparing observed properties of the beam with the established parameters stored in the memory element.

40. The system of claim 39, wherein the processing element further comprises an output means for reporting at least one result of a comparison between observed and stored properties of the beam.

41. A method for measuring the properties of a surgical laser beam comprising:

splitting off a component of the beam for analysis;

directing the component beam onto a photoreactive element having a composition including at least one layer of dye impregnated material having a non-uniform distribution of dye through the layer which reacts in a manner dependent upon an intensity profile of the beam; and detecting changes in the photoreactive element as a measurement of the intensity profile of the laser beam.

42. The method of claim 41, wherein the step of detecting changes in the photoreactive element further comprises capturing an image of the photoreactive element and the method further comprises the step of:

transforming the image into digital data.

43. The method of claim 42 further comprising the step of:

comparing the digital data with stored pre-determined parameters of an ideal beam for a procedure to determine whether the beam is within an acceptable range for the procedure.

44. The method of claim 41, wherein the step of detecting changes in the photoreactive element further comprises capturing an image of the photoreactive element and the method further comprises the step of:

recording the image to provide a record of the intensity profile of the beam simultaneously with a procedure.

45. The method of claim 43 further comprising the step of:

transmitting feed-back signal to a laser controller to modify the laser based on the result of the comparison.

* * * * *